United States Patent [19]

Wetmur et al.

[11] Patent Number: 5,958,681
[45] Date of Patent: Sep. 28, 1999

[54] BRANCH MIGRATION OF NUCLEOTIDES

[75] Inventors: James G. Wetmur, Scarsdale, N.Y.;
Robin S. Quartin, Bedminster, N.J.;
Dean L. Engelhardt, New York, N.Y.

[73] Assignee: Enzo Therapeutics, Inc., New York, N.Y.

[21] Appl. No.: 08/480,000

[22] Filed: Jun. 7, 1995

Related U.S. Application Data

[63] Continuation of application No. 07/499,938, Mar. 26, 1990, abandoned.

[51] Int. Cl.$^6$ .............................. C12Q 1/68; C07H 21/02
[52] U.S. Cl. ................................. 435/6; 536/23.1
[58] Field of Search ...................... 435/6, 91.2; 536/23.1

[56] References Cited

U.S. PATENT DOCUMENTS

| | | | |
|---|---|---|---|
| 4,766,062 | 8/1988 | Diamond et al. | 435/6 |
| 5,124,246 | 6/1992 | Urdea et al. | 435/6 |

FOREIGN PATENT DOCUMENTS

0317077 B1   1/1996   European Pat. Off. .

OTHER PUBLICATIONS

Quartin et al, Biochemistry 28(22) : 8676–8682, 1989.

*Primary Examiner*—Eggerton A. Campbell
*Attorney, Agent, or Firm*—Ronald C. Fedus, Esq.

[57] ABSTRACT

Procedures and compositions for forming and stabilizing non stable branch migrated oligo- and polydeoxynucleotides utilizing a displacer which is either single stranded or partially double stranded and hybridized to a linker strand. The displacer may contain one or more modified nucleotides.

116 Claims, 5 Drawing Sheets

BRANCH MIGRATION OF NUCLEOTIDES

This is a continuation of application Ser. No. 07/499,938, filed on Mar. 26, 1990 abandoned.

BACKGROUND

This invention relates to the formation of stable branch migration structures and the various applications of these structures.

The displacement of one strand of a double-stranded nucleic acid by another single strand with an identical nucleotide sequence is a well documented aspect of DNA or RNA replication and genetic recombination in vivo. Branch points are found in nucleic acids that are undergoing this kind of strand displacement where two strands compete for base pairing interactions with complementary sequences of a third strand. The movement of branch points along the strands of the nucleic acid, branch migration, does not require the action of specific enzymes or proteins.

The phenomenon of branch migration in vitro in the renatured molecules of terminally repetitious, circularly permuted bacteriophage DNA was first reported by Lee, Davis, and Davidson [JMB 48: 1–22 (1970)]. Branched nucleic acid structures suitable for the study of strand displacements can be constructed in vitro using various hybridization conditions.

Branch migration has been exploited to form or resolve DNA-RNA hybrids. In solutions without formamide, a DNA strand will displace RNA from a DNA-RNA hybrid. This reaction is the basis of a homogeneous nucleic acid hybridization assay developed by Vary et al. of Allied Corporation [Nuc. Acids Res. (1987) 15, 6883–6897 and U.S. Pat. No. 4,795,701]. This assay involves RNase digestion of the displaced RNA strand, conversion of AMP to ATP and detection of the product of the conversion by chemiluminescence using luciferase. Vary's method is not applicable to DNA cloning.

In concentrated formamide solutions, a DNA strand may be displaced by RNA to form an R-loop [see Thomas, M., White, R. L., & Davis, R. W. (1976) Proc. Nat. Acad. Sci., USA 73, 2294–2298]. Conceptually, R-loop formation is analogous to the displacement of one DNA strand from the end of a duplex. Regions of double-stranded DNA can take up complementary RNA sequences to form R-loops under conditions where RNA:DNA hybrids are more stable [Casey, J. and Davidson, N. (1977) NAR 4: 1539–1552]. The enrichment of specific DNA sequences has been accomplished using buoyant density sedimentation to select for R-loop structures containing these sequences. The technique of R-loop formation has not been patented. To date, applications of R-looping procedures involve partial denaturation of the target DNA and have not yielded products that can be directly cloned into standard cloning vectors.

D-loop formation that is analogous to R-loop formation can occur between a DNA strand and a superhelical DNA duplex [Radding, C. M., Beattie, K. L., Holloman, W. K., & Wiegand, R. C. (1977) J. Mol. Biol. 116, 825–839]. This reaction depends upon the superhelical free energy and will, thus, not take place with linear DNA molecules. No cloning technology based on this observation has been described. D loop formation in superhelical DNA has been used for specific cleavage [Corey, D. R., Pei, D. & Schultz, P. G. (1989) *J. Am. Chem. Soc.* 111, 8523–8525].

A method has been developed which uses RecA-coated strands to overcome the limitation of D-loop formation to superhelical DNA molecules [Rigas, B., Welcher, A. A., Ward, D. C., & Weissman, S. M. (1986) Proc. Natl. Acad. Sci., USA 83, 9591–9595]. Labeling of the single-stranded probe with biotinylated nucleotides facilitates purification of the D-loop products of this reaction by affinity chromatography. DNA hybrids that contain biotinylated nucleotides have lower melting temperatures than unmodified DNA hybrids, i.e., biotin has a destabilizing effect on the helix [Langer, et al. (1981) Proc. Natl. Acad. Sci. USA 78: 6633–6637]. In this method D-loop formation requires implementation of a pretreatment step to facilitate D-loop formation. Moreover, this procedure does not result in products that are directly clonable into existing DNA cloning vectors.

A short DNA strand hybridized to a longer DNA strand will also be rapidly displaced by a homologous, but longer, overlapping strand in vitro [see Green, C. and Tibbetts, C. (1981) Nuc. Acids Res. 9, 1905–1918]. This observation forms the basis of diagnostic assays for DNA or RNA sequences that are based on branch migration and DNA strand displacement, described in Collins et al. [Mol. & Cell. Probes 2: 15–30 (1988)], Vary et al. [Clin. Chem. 32: 1696–1701 (1986)], U.S. Pat. Nos. 4,766,064 [Williams et al. (1988), Allied Corp.], 4,766,062 [Diamond et al (1988), Allied Corp.], and 4,795,701 [Vary et al (1988), Allied Corp.] and European Patents 0167238 A1 [Collins et al (1985), Allied Corp.] and 0164876 A1[Collins et al. (1985) Allied Corp.].

In these assays, a partially double-stranded probe complex is prepared with a detectable label on one of the two strands. This probe complex is then incubated with a sample containing target nucleic acids (i.e., double-stranded nucleic acids that are at least partially homologous to the single-stranded portion of the probe complex) under appropriate hybridization conditions. The target nucleic acids hybridize to the single-stranded portion of the probe complex and undergo branch migration to release the labeled probe strand. The amount of labeled strand released is proportional to the amount of target DNA in a sample. Thus, this assay involves the use of a pre-formed partially double-stranded probe complex to promote branch migration and relies upon the transient nature of the branch migrated structure and the total release of the labeled probe strand.

In these assays, the efficiency of the strand displacement reaction could be enhanced by the addition of volume excluding reagents, such as polyethers, or by pretreatment of the target with Rec A proteins. Others have also noted that the Rec A protein promotes branch migration that proceeds unidirectionally in the 3'→5' direction [Cox, M. M. & Lehman, I. R. (1981) Proc. Natl. Acad. Sci. USA 78: 6018–6022]. The diagnostic assays developed by the Allied Corp. use pre-formed duplexes to promote displacement and do not relate to the development of genetic engineering techniques or to the stabilization of the branch migration structure.

Thus, the phenomenon of branch migration initiated by the formation of a stable hybrid has been described in the literature. Although the formation of branched or looped structures has been used for identification, purification, and enrichment of DNA sequences, this technique has not been applied to the development of a directly clonable product. Moreover, stabilization of branch migration structures would enhance the efficiency of procedures that involve collection or identification of these entities. Simple methods for preparing stable branch migration structures have not been reported by others.

Experiments described more than 20 years ago showed that the substitution of bromine at position C5 of pyrimidines leads to increased duplex stability [Michelson et al.(1967) Prog. Nuc. Acid Res. & Mol. Bio. 6: 84–141]. Radding et al. [J. Biol. Chem. 116: 2869–2876 (1962)] showed that dG-BrdC is a more thermally stable base pair than dG-dC. In another study, poly dI:poly BrdC had a melting temperature 26° C. higher than poly dI:poly dC [Inman & Baldwin (1964) J. Mol. Bio. 8: 452–469], and it was further shown that poly BrdC displaced poly dC from a poly dI:poly dC duplex to form a new duplex with poly dI [Inman J. Mol. Bio. 9: 624–637 (1964)]. These observations have not been applied to the stabilization of branch migration structures by displacer strands containing modified nucleotide bases.

Tatsumi and Strauss [Nuc. Acids Res. 5: 331–347 (1978)] labeled DNA with bromodeoxyuridine (BrdUrd) in vivo in human lymphoid cells and observed a high degree of branch migration after isolation and shearing of the DNA. These workers suggested that this high level of branch migration reflected the increased stability of helices containing BrdUrd and the trapping of the branch migration configuration. Their results further suggest that once formed, halogen-substituted branch migration structures are relatively stable. Tatsumi and Strauss did not investigate the phenomenon of branch migration in vitro, did not use synthetic oligo- or polynucleotides labeled with halogenated nucleotides, i.e., pre-modified displacer strands, in their experiments, and could not use the branch migration structures resulting from their experiments for purposes of cloning or mutagenesis.

Currently, specific DNA fragments derived from genomic DNA are usually identified using Southern blot analysis of the restriction enzyme digestion products of that genomic DNA. Southern blot analysis of DNA is a multi-step procedure that generally involves the use of radioisotopes and autoradiography for fragment identification following electrophoresis, transfer of the electrophoresced products to a nitrocellulose or nylon membrane, and hybridization of the transferred products to sequence-specific DNA probes. Procedures that provide for simultaneous labeling and identification of specific DNA fragments would be significantly simpler, faster, and cheaper than Southern blot analyses and would have a significant impact on the field of genetic engineering.

Labeling of DNA sequences has come to imply the incorporation of modified nucleotides at internal or terminal positions. Often this is accomplished enzymatically using nucleotides labeled with small compounds such as biotin, sulfhydryl groups, mercury, allylamine, and digoxigenin. Enrichment or purification of these labeled nucleic acids can be accomplished by affinity chromatography. For example, biotinylated DNA, including D loops, can be selectively bound and eluted from solid matrices bearing avidin or streptavidin groups, as has been reported by Ward and his co-workers [Langer, op. cit.]. Similarly, DNA labeled with sulfhydryls can be purified by affinity chromatography on mercurated agarose and mercurated DNA can be purified based on its affinity for sulfhydryl groups. The enrichment of mRNA from total RNA populations can be accomplished based on the affinity of the polyA tails on the messengers for oligo-dT matrices. Following their purification, these enriched or purified nucleic acid sequences are often further subjected to a series of procedures that render them clonable. Labeling procedures that permit sequence enrichment or purification by affinity chromatography and then the direct cloning of these enriched or purified fractions would have significant advantages over existing techniques.

The identification or enrichment of a specific subset of nucleotide sequences or of DNA fragments in isolated genomic DNA or total populations of RNA for the express purpose of cloning those sequences or fragments has been accomplished by a variety of methods that include, but are not limited to those involving the selection of DNA fragments capable of undergoing branch migration, R-loop, or D-loop formation. Selective cloning of fragments in a population has been achieved based on restriction endonuclease cleavage sites, especially those that recognize a unique site [Brown. N. L. & Smith, M. (1977) Proc. Natl. Acad. Sci. U.S.A. 74, 3213–3216]. and size [Thomas, M., Cameron, J. R. & Davis, R. W. (1974) Proc. Natl. Acad. Sci. U.S.A. 71, 4579–4583]. Although these strategies have been used widely and successfully to clone a wide variety of genes, they are not universal and have limited specificity.

Another application of genetic engineering techniques relates to the modification of genetic material so as to add or delete nucleotide bases, such as for therapeutic purposes. Efforts to either replace, inactivate, or modify genetic material are currently in progress. In higher eukaryotic organisms, the approaches taken have, thus far, required that the agents used to bring about these changes be incorporated into various plasmid vectors that contain all or part of various viral genomes. Site-directed gene replacement in lower eukaryotes, such as yeasts, has been accomplished. A serious deterrent to the therapeutic manipulation of human genetic material in vivo relates to the lack of a suitable, benign vector system. The ability to perform targeted delivery and incorporation of genetic material into chromosomal DNA without using a viral vector would represent a major advance in the field of gene therapy.

Green and Tibbetts [op. cit.] expressed an interest in using branched DNA structures for in vitro site-directed mutagenesis and, in fact, were able to use stable D-loop structures in superhelical DNA for target deletion mutagenesis [Proc. Natl. Acad. Sci. USA 77: 2455–2459 (1980)]. They were unable to achieve this goal with linear target DNA molecules using the branch migrated structures they obtained from in vivo labeling of cells with BrdUrd (see Green and Tibbetts, 1981, op. cit.) due to the short half-lives of their branched structures.

Site-specific genetic manipulation has been described [Capecchi, M. R. (1989) Science 244, 1288–1292] where a small proportion of the DNA which becomes integrated into the host genome is directed, by homologous recombination, to the desired target DNA. Unfortunately, the additional integration events occur at random and may inactivate or activate genes leading to deleterious consequences. Sequences of DNA capable of initiating triple-helix formation have been reported. [Francois, J. C., Saison-Behmoaras, T., Thoung, N. T. & Helene, V. (1989) Biochemistry 28, 9617–9619; Povsic, T. J. & Dervan, P. B. (1989) J. Am. Chem. Soc. 111, 3059–3061]. The utilization of triple helix formation as an adjunct to site-specific genetic manipulation is unknown in the art.

SUMMARY

In its most general terms our invention relates to techniques which increase the probability of certain types of reactions proceeding in a desired manner. Our techniques promote specificity of reaction and provide simple methods for preparing stable branch migration structures.

procedures for simultaneous labeling and identification of specific DNA fragments that are significantly simpler, faster, and cheaper than Southern blot analyses.

labeling procedures that permit sequence enrichment or purification by affinity chromatography and selective cloning.

a method of performing targeted delivery and incorporation of genetic material into chromosomal DNA without using a viral vector.

Branch migration is the process by which a single strand of nucleic acid is inserted and replaces at least a portion of one strand of a nucleic acid duplex. Branch migration is a useful technique for the sequence-dependent attachment (capture) of an oligodeoxynucleotide duplex containing a single-stranded tall into the end of a deoxynucleotide molecule, or of the sequence dependent incorporation of an oligodeoxynucleotide into a deoxynucleotide molecule at a location other than at its end. Existing methods require the formation of a stable hybrid prior to the initiation of branch migration; our process allows initiation and formation of a branch migrated complex without prior stabilization. We have achieved this result by stabilizing the resulting branch migrated complex concurrently with formation or thereafter, or both.

Our specific attachment procedure may be used (A) to label a particular fragment for detection without blotting and subsequent hybridization, (B) to mark a particular fragment for affinity chromatography, (C) to facilitate cloning by introducing a new 5' or 3' overhang compatible with a restriction endonuclease site in a cloning vector, or (D) for other purposes which will become apparent from the present disclosure.

The various methods and materials of our invention require a displacer entity which is at least partially complementary to and is capable of binding to a target. Both the displacer and target are oligo- or polynucleotide sequences, either synthetic or naturally occurring. Our novel displacer may be used as a single stranded entity in certain embodiments of our invention; in other embodiments it is utilized as a partially double stranded entity hybridized to a linker strand.

One embodiment of our invention provides a novel displacer-linker duplex and an improved method of attaching a deoxynucleotide displacer sequence to a strand of a target deoxynucleotide duplex. The oligo- or polydeoxynucleotide displacer-linker duplexes of our invention consist of two strands, a displacer strand and a linker strand. The displacer strand contains a sequence of nucleotides at least partially complementary to the linker strand and a sequence at least partially complementary to one strand of a recipient polydeoxynucleotide duplex.

The sequence-dependent attachment (capture) of an oligodeoxynucleotide duplex containing a single-stranded tail can be influenced by branch migration into the end of a DNA molecule. Our novel oligo- or polydeoxynucleotide displacer-linker duplex is capable of initiating branch migration at the end of a recipient polydeoxynucleotide duplex without the prior formation of a stable hybrid with such recipient polydeoxynucleotide duplex. More particularly, these novel duplexes can hybridize to and initiate branch migration at a restriction endonuclease cleavage site, in particular adjacent to a 3' or 5' single stranded extension on a recipient polydeoxynucleotide duplex.

Substitution of one or more of the nucleotides in the portion of the displacer strand which is complementary to the recipient increases DNA—DNA hybrid stability. Oligonucleotides containing the modified nucleotide displace non-modified nucleotide containing strands from the ends of duplexes. In the case of 3' or 5' overhangs the rate of displacement is of the same order of magnitude as the nucleation reaction of DNA reassociation.

We also provide a displacer which is not hybridized to a linker strand and which is capable of initiating triple helix formation. This class of displacers comprises 1. a first sequence which is capable of initiating triple helix formation, and which comprises
   a) at least six consecutive pyrimidine bases or
   b) at least seven bases where at least six of the bases are pyrimidine bases and the seventh base is guanine, and
2. a second sequence proximate to such first sequence which is
   a) complementary to and runs antiparallel to the second strand of the recipient duplex and
   b) which is capable of initiating branch migration proximate to the triple helix.

We further disclose displacers which are nuclease resistant and the method of modifying a recipient duplex to confer nuclease resistance to the duplex. These displacers contain at least one moiety attached to a terminus of the oligo- or polynucleotide, which moiety confers endonuclease resistance to the terminus to which it is attached.

We have found it desirable to modify at least one of the nucleotides in the displacer strand which is at least partially complementary to one strand of the recipient polydeoxynucleotide duplex. The nucleotide is modified in a manner that increases the stability of the hybrid displacer-recipient duplex.

In addition to stability increasing modifications, we have found it useful to incorporate modified nucleotides in the displacer or linker which permit detection of the displacer-recipient hybrid or its isolation by affinity chromatography.

Another aspect of our invention is the hybrid structure formed when the displacer or displacer-linker duplex is attached to the target. Where the hybrid is the result of the attachment of the target to our novel displacer-linker duplex, the linker strand is preferably covalently linked to one of the strands of the recipient duplex.

In a preferred version of our invention, the hybrid structure containing the attached displacer sequence of single stranded deoxynucleotide is stabilized, most desirably by the presence of at least one modified nucleotide in the displacer strand.

We also disclose a labelled hybrid structure. This labelled hybrid structure incorporating our displacer-linker is useful in many biochemical procedures, such as, for example, to facilitate capture of the displacer-recipient hybrid by affinity chromatography, to label one end of an cloned deoxynucleotide insert in a vector, to facilitate restriction endonuclease mapping of an insert, to facilitate selectively cloning a recipient polynucleotide duplex and to facilitate isolation of clones of contiguous polydeoxyribonucleotides. The hybrid incorporating the displacer is useful in affinity chromatography and to facilitate 1] detection of specific oligo- or polynucleotides and 2] site specific genetic manipulation Our methods involve the stabilization of a non stable complex between one strand of a recipient polydeoxynucleotide sequence and a displacer sequence of single stranded DNA where the displacer sequence is at least partially complementary to such strand of a recipient polydeoxynucleotide sequence. The complex may be stabilized by
   a) the presence of at least one modified nucleotide in the displacer strand,
   b) forming a DNA triplex between the displacer sequence and the recipient duplex,
   c) providing a displacer strand comprising a nucleotide sequence and a sequence specific DNA binding moiety that does not significantly melt the recipient DNA duplex at the site to which it attaches,
   d) attaching the displacer to a linker prior to or concurrent with attachment to the target duplex and thereafter covalently attaching the linker to the second strand of the target duplex, or e) a combination of procedures a) and d) or c) and d).

DESCRIPTION OF SPECIFIC EMBODIMENTS

Our process allows initiation and formation of a branch migrated complex without prior stabilization. We have achieved this result by stabilizing the resulting branch migrated complex concurrently with formation or thereafter, or both.

In one embodiment of our invention a displacer, a linker, a displacer-linker duplex and an improved method of attaching a deoxynucleotide displacer sequence to the end of a strand of a target deoxynucleotide duplex utilizing branch migration are utilized to prepare branch migrated complexes. This procedure requires the use of oligo- or polydeoxynucleotide displacer-linker duplexes consisting of two strands; a displacer strand and a linker strand.

The displacer strand of the displacer-linker duplex contains a sequence of nucleotides at least partially complementary to a linker strand. The displacer strand is capable of hybridizing to the linker strand and has an overhang at its 3', 5' or both ends. The overhang at one end of the displacer strand will comprise a deoxynucleotide sequence at least partially complementary to one strand of a recipient polydeoxynucleotide duplex.

The presence of an incorrect (non-complementary) nucleotide in the portion of the displacer strand at least partially complementary to the duplex limits branch migration beyond the point of the mismatch. Thus, the initial portion of the overhang of the displacer strand must be complementary to the recipient strand and this complementarity to the recipient must extend over a sufficient number of nucleotide bases to allow formation of at least a transient branch migrated complex with the recipient duplex required for the formation. In the transient branch migrated structure the stability of the structure increases as the number of bases increases. There is no minimum number of bases required for the initiation and formation of the branch migrated structure. It is desirable to have at least the first three (3) bases complementary, preferably at least the first five (5) bases complementary to the recipient.

The opposite end of the displacer strand may be blunt with relation to the linker strand after hybridization to it or either the displacer strand or the linker strand may have an overhang. In one embodiment, one of the linker or displacer strands will have an overhang complementary to an overhang resulting from cleavage by a restriction endonuclease.

The linker strand may be of any size provided only that it is of sufficient size to hybridize to the displacer. It is desirable that the linker be in the range of 10–20 bases in length. In a preferred embodiment of our invention, one end of the linker is covalently linked to one strand of the recipient after branch migration occurs.

The displacer strand may be hybridized to the linker strand prior to or after reaction of the displacer with the recipient.

As stated above, prior formation of a stable hybrid between our displacers and a recipient polydeoxynucleotide duplex is not required. Any oligo- or polydeoxynucleotide displacer-linker duplex which is capable of initiating branch migration at the end of a recipient polydeoxynucleotide duplex can be used in our process. Once branch migration has been initiated, our techniques of stabilization concurrent with or subsequent to formation of the branch migrated structure will maintain the complex in its branched form.

Our displacer-linker duplexes are capable of instituting branch migration at any type of end of a recipient polydeoxynucleotide duplex, such as blunt ends or at ends formed by mechanical shearing. In preferred embodiments, our novel duplexes hybridize to and initiate branch migration at a restriction endonuclease cleavage site, most effectively adjacent to a 3' or 5' single stranded extension on a recipient polydeoxynucleotide duplex.

We have discovered that modifying the nucleotides in the sequence of the displacer which is at last partially complementary to the target increases the stability of the branch migrated complex. Those modifications which increase the association constant with the complementary deoxynucleotide by at least about 20 percent provide useful results. We prefer those modifications which increase the association constant by at least about 70 percent.

To stabilize the complex concurrent with formation, one or more, preferably at least about 10 percent of the nucleotides in the sequence of the displacer which is at least partially complementary to the target, are modified.

Specific modifications which we have found to work well in our invention include those selected from 5-halogenated pyrimidine nucleotides, 5-methyldeoxycytidine, diaminopurine deoxynucleotide, ribonucleotides, and 2'-alkylated ribonucleotides. 5-bromodeoxyuridine or 5-methyldeoxycytidine provide the best results.

Alternatively, the complex may be stabilized after branch migration has occurred. In this embodiment, the linker of the branch migrated complex is covalently attached to one strand of the reagent duplex. Preferably the branch migration complex is incubated with a ligase. The covalently linked linker strand prevents the uncoupling of the branch migrated structure.

In a preferred embodiment of our invention, the branch migrated structure is stabilized by a combination of concurrent and subsequent stabilization techniques, utilizing modified nucleotides and covalent linkage.

Our displacer-linker may be modified by incorporation of a label to allow detection of the hybrid construct. Any modification which permits detection and which does not disrupt the branch migrated complex may be used. Common detection modifications are radioactive labels, fluorescent and chemiluminescent labels, enzymes and targets for detection, including, by way of non-limiting example, biotin moieties, phosphorothioate linkages and antigens. For details on the use of various labels and detection systems see, e.g. Keller, G. H., et al., DNA Probes (1989) and Piper, M. A., et al., Nucleic Acid Probes (1989).

In another embodiment, our single stranded displacers are not hybridized to a linker strand and are capable of initiating triplex formation at a point other than at the end of a recipient polynucleotide. This class of displacers comprises
1. a first sequence which is capable of initiating triple helix formation, and which comprises
   a) at least six consecutive pyrimidine bases or
   b) at least seven bases where at least six of the bases are pyrimidine bases and the seventh base is guanine, and
2. a second sequence proximate to such first sequence which is
   a) complementary to and runs antiparallel to the second strand of the recipient duplex and
which are capable of initiating branch migration proximate to the triple helix.

In one embodiment of our invention, the second sequence is adjacent to the first sequence. In another embodiment the second sequence is separated from the first sequence by intervening moieties. In this embodiment, we prefer separation by 1 to 5 intervening moieties.

Intervening moieties may be selected from any moiety which when interposed between the first and second sequence will not abolish the coordinate function of the two sequences. Examples are intercalating agents and agents that function to diminish the rigidity of the nucleotide sequence, thereby facilitating the hybridization of the complementary sequence to the antiparallel strand. Such moieties include moieties containing sugar phosphate linkages. In a preferred embodiment, the intervening moieties are nucleotides. The nucleotides may be modified nucleotide. Useful modified nucleotides include those having an intercalating agent covalently attached and modified nucleotides incapable of base pairing.

Once the displacer hybridizes with the antiparallel strand it is desirable to increase the stability of the complex. We have found that we are able to increase the stability by modifying at least one of the nucleotides in the displacer strand prior to hybridization. The nucleotide is modified in a manner that increases the stability of the hybrid displacer-recipient duplex. The modification may be in either the first sequence which is capable of initiating formation of the complex, or in the second sequence proximate to such first sequence and which is complementary to and runs antiparallel to the second strand of the recipient duplex.

When the modification is in the first sequence it is preferably selected from the group consisting of modified nucleotides which increase the association constant with the complementary deoxynucleotide by at least about 20 percent, preferably at least about 70 percent. Representative non-limiting examples of such modified nucleotides include 5-halogenated pyrimidine nucleotides. Most preferably, the modified nucleotide is selected from the group consisting of 5-bromodeoxyuridine and 5-methyldeoxycytidine.

When the modification is in the second sequence it may be selected from the group consisting of 5-halogenated pyrimidine nucleotides, 5-methyldeoxycytidine, diaminopurine deoxynucleotide, ribonucleotides and a 2'-alkylated ribonucleotides. Preferably the modified nucleotide is a 5-halogenated pyrimidine nucleotide, especially 5-bromodeoxycytidine, or 5-methyldeoxycytidine.

In addition to the stability increasing modification, we have found it useful to incorporate modified nucleotides in the displacer which permit detection of the displacer-recipient hybrid. Suitable modifications may be selected from the group comprising radioactive labels, fluorescent and chemiluminescent labels, enzymes and targets for detection, including, by way of non-limiting example, biotin moieties, phosphorothioate linkages and antigens.

We have also developed displacers which are exonuclease resistant. These nuclease resistant displacers are suitable for use in cell culture and living organisms. These displacers contain at least one moiety conferring exonuclease resistance attached at or near the terminal nucleotide of the displacer.

The moiety conferring nuclease resistance may be attached to the deoxyribose moiety at the hydroxyl group or the phosphate moiety of a terminal nucleotide.

The moiety conferring nuclease resistance may be selected from the group consisting of intercalating agents, isoureas, carbodiimides and N-hydroxybenzotriazoles, polypeptides and proteins.

A preferred moiety is when the group is attached to the hydroxyl group is a methylthiophosphonate.

A modified or unmodified 2',3' dideoxyribose nucleotide attached to the 3'-terminal deoxyribonucleotide through a phosphodiester linkage is useful for conferring resistance at the 3' end.

The formation of complexes utilizing either our single stranded displacer or our displacer-linker proceeds in accordance with well known principles. [Maniatis, et al., (1982) Molecular Cloning (New York: Cold Spring Harbor Laboratories].

One of the significant uses of our invention is for the site specific addition or deletion of nucleotides in a recipient polydeoxynucleotide sequence. This process occurs when the new strand is introduced to the recipient duplex and displaces the original strand. The cellular machinery involved in generalized recombination and gene conversion will act to transfer sequence information from the displacer strand to the recipient polydeoxynucleotide. For a review of possible mechanisms for this transfer see Stahl, F. W., Genetic Recombination (1979).

The following Examples are set forth to illustrate various aspects of the present invention but are not intended to limit in any way its scope as more particularly set forth in the claims.

EXAMPLES

Example 1

Preparation of Labeled Displacer and Linker Strands

The sequences of the oligonucleotides used in this example, as well as in the other examples provided, are listed in Table I. These oligonucleotides were synthesized on an Applied Biosystems Model 380B DNA Synthesizer using standard phosphoramidite chemistry, but any other standard method for synthesizing oligonucleotides would work as well for this invention.

The bromodeoxycytidine (BrdC) and the methyldeoxycytidine (MedC)-containing displacer strands used in these examples were prepared by incorporation of 5-bromodeoxycytidine or 5-methyl deoxycytidine phosphoramidite monomers into the oligonucleotides during their synthesis. Purification steps were limited to hydrolysis of base-protecting groups and cleavage from the support with $NH_4OH$, evaporation, resuspension and ethanol precipitation. All oligodeoxynucleotides were 5'-labeled with $^{32}P$ using T4 polynucleotide kinase, subjected to polyacrylamide gel electrophoresis on 20% acrylamide-8M urea gels, and visualized by autoradiography. A single oligodeoxynucleotide species of the correct size was routinely detected.

To measure capture at recipient ends with 3' or 5' overhangs, linker or displacer oligodeoxynucleotides, respectively, were labeled with $^{32}P$ using T4 polynucleotide kinase. The reaction of linkers, but not displacers, with labeled ATP was followed by reaction with excess unlabeled ATP to ensure that all linker strands contained a 5'-phosphate. The oligodeoxynucleotides were purified over spun columns of Sephadex G-50 [Maniatis, et al., (1982) Molecular Cloning (New York: Cold Spring Harbor Laboratories].

Example 2

Stability of BrdC-Containing Hybrids

Melting temperatures for oligodeoxynucleotides were determined as described by Quartin & Wetmur [Biochem. 28:1040–47 (1989)]. Briefly, complementary oligodeoxynucleotides were mixed in equal molar ratios in either 6×SSC, pH 4.0, 6×SSC, pH 7.0, or in 1 M NaCl, 0.05 M borate, 0.2 mM EDTA, pH 10, then placed in a 1 cm quartz cuvette. Solutions were heated in the cuvettes at 0.3° C./minute in a Beckman Model 25 spectrophotometer equipped with a water-jacketed cell holder. The solution temperature was monitored using a thermistor attached to the cell holder. Hyperchromicities for all duplexes tested were 21%. The concentration-dependent melting temperatures (Tm=tm+273.16) were calculated according to the method of Marky and Breslauer [Biopolymers 26: 1601–1620 (1987)]. Tm values reported are reliable to ±1° C.

The tm values for dC-containing oligodeoxynucleotides and for their BrdC and MedC-containing analogs are presented in Table II. The substitution of BrdC or MedC for dC leads to an increase in melting temperature ΔTm=Tm'–Tm, where Tm and Tm' are the melting temperatures for dC- and BrdC- or MedC-containing oligodeoxynucleotides, respectively.

These results indicate that duplexes containing oligonucleotides with BrdC or MedC are more stable than those with only dC.

The association constant for the modified nucleotide, BrdC or MedC, relative to the association constant for dC, base pairing with complementary dG, may be approximated by $$K=e^{-\Delta H^\circ \Delta Tm/(RTn^2 Ns)}$$

where
ΔH°=enthalpy for formation of the oligodeoxynucleotide duplex
R=gas constant
Tn=average of Tm and TM' and
Ns=number of modified nucleotides.

Based on this analysis, the association constant 13 increased about 70–90% for BrdC substitution and about 50–70% for MedC substitution.

Example 3

Displacement By BrdC

A gel migration assay was used to monitor the displacement of 5'-$^{32}$P-labeled dC-containing oligodeoxynucleotides from unlabeled complementary oligodeoxynucleotides by their BrdC-containing analogs.

Labeled dC-containing oligodeoxynucleotides were annealed to unlabeled dC-containing complementary strands at room temperature in 1 M NaCl at concentrations of 1 and 3 μg/ml, respectively, and then brought to 4° C. BrdC-containing analogs of the labeled strands (at concentrations ranging from 3 to 400 μg/ml were incubated with dC-containing duplexes as a function of time at various temperatures. Aliquots taken at each time point were diluted into electrophoresis loading buffer and stored at −70° C. prior to electrophoresis. Samples were loaded onto a 20% acrylamide gel in 2.5% ficoll 400, and electrophoresis was performed at 4° C. at 400 volts, 5–15 milliamps in 89 mM TrisHCl, 89 mM borate, 1 mM EDTA, pH 8 (TBE). The gels were dried and subjected to autoradiography.

The rates at which oligonucleotides containing BrdC displace those containing dC are summarized in Table III. Reactions initiated at blunt ends proceed faster as the temperature increases due to increased breathing at the blunt ends. Displacement reactions where initiation occurred at four base overhangs were more than two orders of magnitude faster than reactions initiated at blunt ends. The stability of a duplex formed between the displacing strand and the overhang of a performed duplex increased with decreasing temperature. Thus, in the temperature range of 22 to 37° C., the rate of displacement decreases with increasing temperature.

These results demonstrate that oligonucleotides containing BrdC displace the dC analogs in a time- and temperature-dependent reaction, even at blunt-ended recipients.

The effect of including a linker strand in displacement reactions was investigated at both 3' and 5' 4-base overhangs with G+C content of 0–100%.

These results demonstrate that displacement rates using displacer-linker duplexes are at least 8-fold faster than displacement rates using only displacer oligodeoxynucleotides. Based on these results we conclude that the methods described in Examples 7–8 are not restricted by the rate of association of displacer—linker duplexes and recipient duplexes.

Example 4

Hybridization of the Displacer to Target DNA

The BrdC- or MedC-containing displacer strand is hybridized to the complementary strand of a double-stranded target DNA in the absence of a linker. Linkers complementary to a portion of the target DNA are added subsequent to this hybridization step, if desired.

Figure 1A:
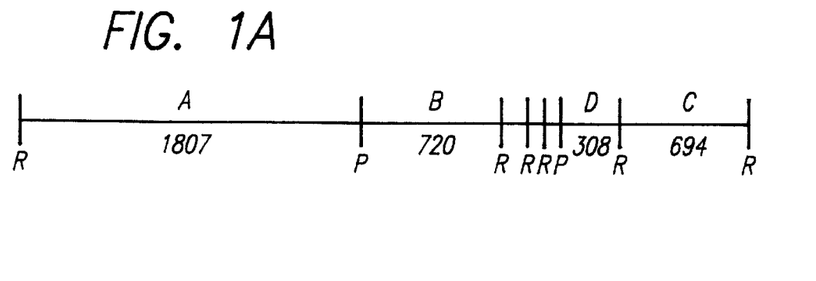
FIG. 1(A) depicts a restriction map of pALA-D. R=RsaI, P=PstI. Fragments A–D are labeled above the line, with the nucleotide lengths indicated beneath. There is a single SmaI site in fragment D. (B) Branch migration of displacer (open rectangle), bound to linker (filled rectangle), into a recipient duplex with a four base 3'-overhang (PstI end of fragment FIG. 1(B) shows the conversion between the duplex bound to the 3' overhang only (left) and following complete branch migration (right).

The target DNA used in Examples 4–9 was plasmid pALA-D, a pUC9 expression vector containing the cDNA sequence of human delta-aminolevulinate dehydratase (ALA-D) [Wetmur, et al. (1986), Proc. Natl. Acad. Sci., USA 83: 7703–7707].

pALA-D was digested with RsaI and PstI to yield seven fragments, four of which contain one PstI end with a 3'-overhang and one blunt RsaI fragment (FIG. 1A). The standard displacer sequence, P-D-dC, is complementary to the first 24 nucleotides of the 3'-overhanging strand of the PstI end of restriction fragment B. Initiation of displacer hybridization to the recipient target duplex begins with base pairing of the displacer with the four base overhang of the PstI site. The displacer may replace all or part of the homologous portion of the recipient duplex strand by single-stranded DNA branch migration.

The digested pALA-D DNA (20 μg/ml) is mixed with the 34-mer displacer DNA (6 μg/ml) in a ptI-reduced T4 DNA ligase buffer [50 mM Tris-HCl, pH 7.0, 1 mM ATP, 10 mM MgCl$_2$, 20 mM Dithiothreitol (DTT), 50 μg/ml bovine serum albumin (BSA)], incubated at 55° C. for 10 min., then cooled to room temperature.

Figure 1B:
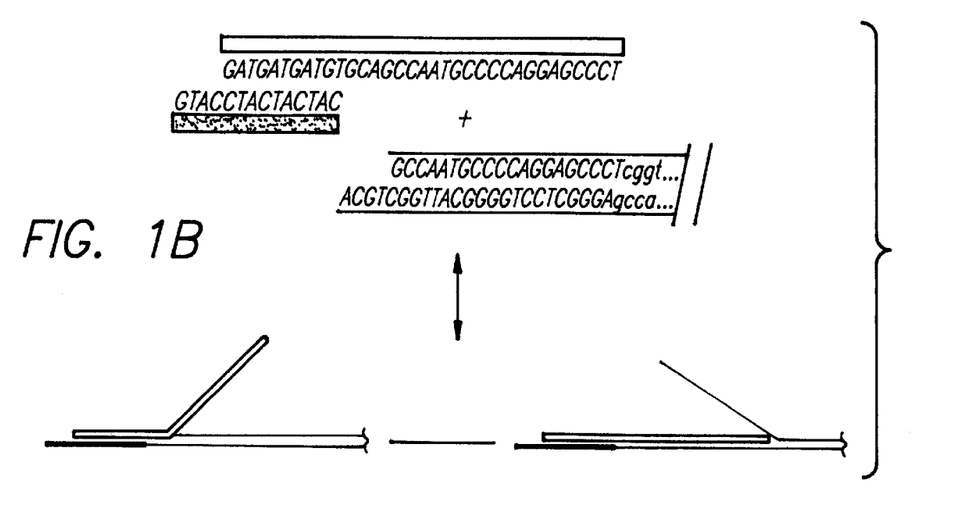
Figure 1C:
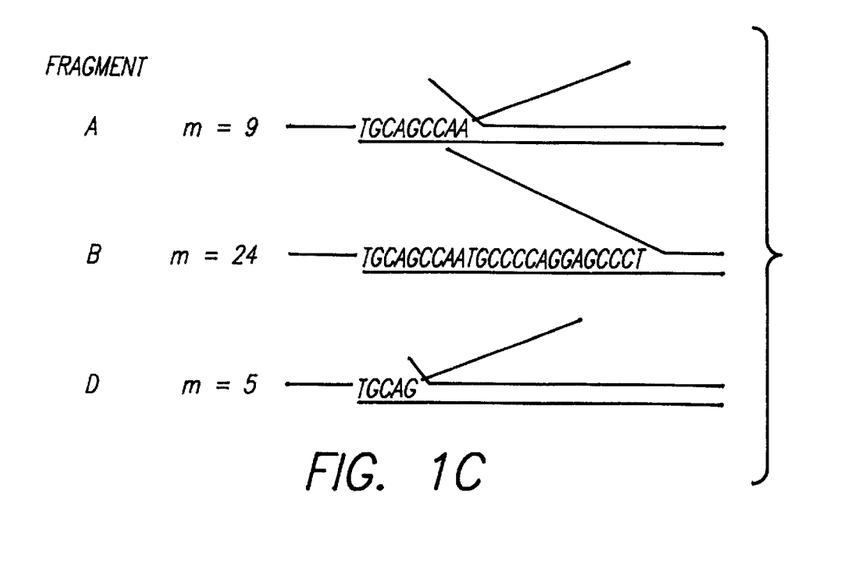
FIG. 1(C) depicts the maximum displacement with specific pALA-D fragments. m=the maximum number of base pairs which can be formed between the displacer and the complementary recipient strand.

FIG. 1C shows the potential for branch migration of the displacer into pALA-D fragments with one Pst I and one blunt (RsaI) end. For fragment B, where there is full complementarity to the displacer, the maximum number of displacer-recipient base pairs (m) is 24. The maximum number of branch migration steps is (m-4) because four base pairs are formed between the displacer and the 3' PstI overhang. Fragment D and the smallest (71 base pair) PstI-RsaI fragments contain no complementarity beyond the PstI site. Thus, m=5, including the four base overhang and one branch migration step. Fragment A contains four additional nucleotides adjacent to the PstI site which are complementary to the displacer. Thus, m=9, including the four overhang and five branch migration steps. Unlike fragment B, where branch migration may go to completion, all branch migration structures with fragments A and D contain two single-stranded branches.

Example 5

Hybridization of the Displacer to Target DNA in the Presence of the Linker

In a second embodiment of this invention, branch migration-mediated capture of linker oligodeoxynucleotides was performed according to the scheme in FIG. 1B. In this embodiment, the recipient target duplex, the displacer oligodeoxynucleotides, and the linker deoxyoligonucleotides are all present during the hybridization reaction. The linker sequence, 5'-$^{32}$P-labeled P-L-dC, forms a duplex with the 5' portion of the displacer sequence which lacks homology to the recipient duplex. The displacer-linker duplex formed displaces the homologous target strand by base pairing to the recipient target strand.

pALA-D was digested with PstI and RsaI. Digested plasmid (20 μg/ml) was mixed with a 34-mer displacer oligodeoxynucleotide (6 μg/ml) and a 5'-$^{32}$P-labeled 14-mer linker oligodeoxynucleotide (2 μg/ml) in a pH-reduced T4 DNA ligase buffer [50 mM Tris-HCl, pH 7.0, 1 mM ATP, 10 mM MgCl$_2$, 20 mM Dithiothreitol (DTT), 50 μg/ml bovine serum albumin (BSA)], incubated at 55° C. for 10 min., then cooled to room temperature.

Example 6

Formation of the Displacer-Linker Duplex

In another embodiment of this invention, the initial step of the displacement reaction involves the formation of a displacer-linker duplex and the subsequent addition of this displacer-linker duplex to a target duplex.

Formation of the displacer-linker duplex may be accomplished in the following way. A 34-mer displacer oligodeoxynucleotide (6 μg/ml) is mixed with 5'-$^{32}$P-labeled 14-mer linker oligodeoxynucleotide (2 μg/ml) in a pH-reduced T4 DNA ligase buffer [50 mM Tris-HCl, pH 7.0, 1 mM ATP, 10 mM MgCl$_2$, 20 mM Dithiothreitol (DTT), 50 μg/ml bovine serum albumin (BSA)], incubated at 55° C. for 10 min., then cooled to room temperature.

Example 7

Hybridization of the Displacer-Linker Duplex to the Target DNA pALA-D is digested with PstI and RsaI to yield 7 restriction fragments. The digested pALA-D DNA (40 μg/ml) in 50 mM Tris-HCl, pH 7.0, 1 mM ATP, 10 mM MgCl$_2$, 20 mM DTT, 50 μg/ml BSA is mixed with an equal volume of the displacer-linker duplex prepared in Example 6. This mixture is incubated at 55° C. for 10 min., then cooled to room temperature.

Example 8

Ligation of the Linker Oligodeoxynucleotide to the Target Strand

Figure 2:
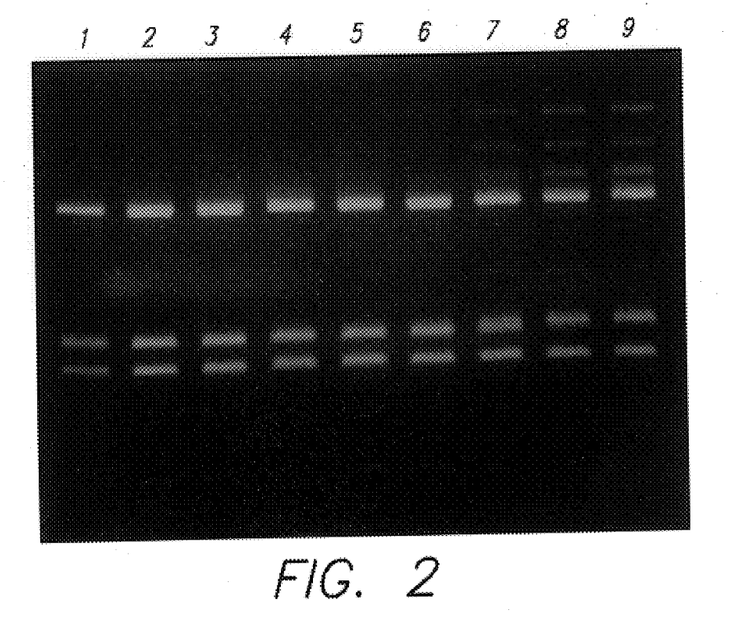
FIG. 2 depicts the capture reaction of P-D-BrdC plus P-L-dC. UV fluorogram of 1% agarose gel. Lane 1: RsaI/PstI digested pALA-D (200 mg). A, B, C, and D refer to fragments shown in FIG. 1. Lanes 2–9: products following ligation in the presence of P-D-BrdC (6 µg/ml), P-L-dC (2 µg/ml), and 5 U/ml ligase for 1, 2, 4, 8, 16, 32, 64, and 128 min, respectively.
Figure 3:
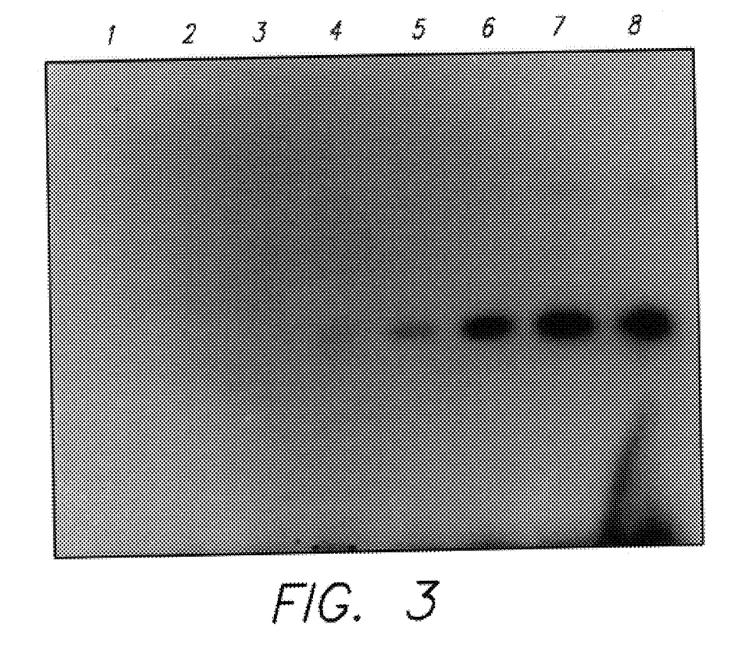
FIG. 3 depicts the autoradiogram of FIG. 2. Lanes 1–8 correspond to the radiolabeled lanes 2–9 of FIG. 2.

The efficiency and the specificity of the branch mediated linker ligation reaction is demonstrated in FIGS. 2 and 3.

The time requirements for the ligation of the pALA-D PstI-RsaI fragments in the presence of the displacer P-D-BrdC (6 μg/ml) and the linker P-L-dC (2 μg/ml) were established using T4 DNA ligase (5 U/ml ligase) and incubation times ranging from 1–128 min. The results are illustrated in FIG. 3, lanes 2–9. Ligation results in a small, time dependent decrease in the mobility of fragment B. The ligation of the linker to the branch migrated structure is 50% completed in 32 min. and 100% completed within approximately 1 hr. A similar experiment carried out using 25 U/ml ligase proceeded 50% to completion in 8 min. Thus, the reaction rate for this ligation reaction was linearly dependent on ligase concentration and time. These results show that branch mediated ligation of a linker oligonucleotide is an efficient reaction that occurs fairly rapidly.

FIG. 3 is an autoradiogram of the gel shown in FIG. 2 and illustrates the detection of ligation of 5'-$^{32}$P-labeled linkers to the recipient fragments. Under conditions where the reaction with fragment B (m=24) is carried to completion, fragment A (m=9) is barely visible and fragment D (m=5) is undetectable. The majority of the labeled linkers are associated with fragment B. These results demonstrate the specificity of branch mediated linker capture.

Example 9

Specificity of the Branch Migration Reaction

Figure 4A:
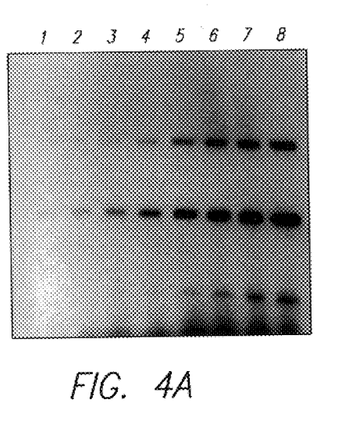
FIG. 4(A) depicts an autoradiogram similar to FIG. 3, but with higher ligase concentration and P-D-dC replacing P-D-BrdC.

The requirement of BrdC- or MedC-containing displacer strands for specific and efficient branch migration-mediated linker capture is illustrated in the following experiment. FIG. 4A shows an autoradiogram analogous to that presented in FIG. 3, where the displacer strand is P-D-dC instead of P-D-BrdC Under conditions where the reaction with fragment B is carried 50% to completion, both fragment A and Fragment D were easily detected. Table IV contains relative autoradiographic intensities for fragments A, B and D, using P-D-BrdC, P-D-MedC and P-D-dC as displacer molecules. The intensity of fragment D was assigned the value of 1. Since the intensities for fragments A and B were determined using a 2-fold time course assay, they are reliable to +/−50%. The data in Table IV demonstrate that the use of BrdC or MedC in the displacer is important for obtaining highly specific branch migration-mediated capture.

Figure 4B:
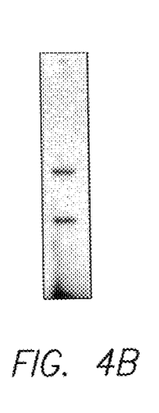
FIG. 4(B) depicts the an early time point in an autoradiogram identical to FIG. 3 except using P-D-BrdC-E(10) replacing P-D-BrdC.

Displacer P-D-BrdC-B(10) was synthesized with one incorrect nucleotide such that only 9 base pairs could be formed between the displacer and the complementary recipient strand prior to the mismatch. FIG. 4B is an autoradiogram of a branch migration-mediated capture reaction carried out under conditions leading to trace levels of capture. The intensity ratios are given in Table V. The capture by fragment B (m=24 with mismatch at 10) was exactly the same as that of fragment A (m=9). Thus, a single mismatch at position 10 blocked subsequent branch migration, indicating that the branch migration reaction is extremely specific.

Figure 4C:
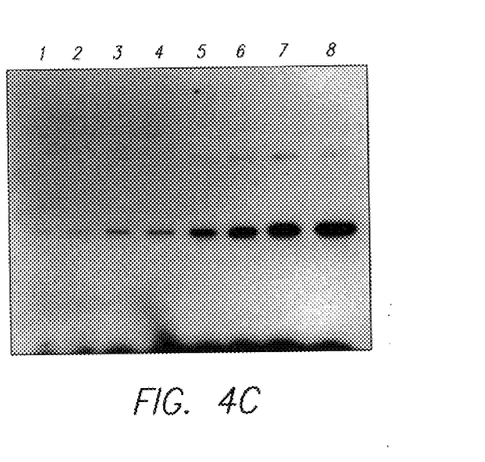
FIG. 4(C) depicts an autoradiogram identical to FIG. 3 except using P-D-BrdC-E(24) replacing P-D-BrdC.

FIG. 4C shows an autoradiogram analogous to that in FIG. 3, where the displacer was P-D-BrdC-B(24). The final nucleotide of P-D-BrdC-B(24) differed from that of P-D-BrdC. The results were similar to those in FIG. 3. Thus, the formation of the final singly-branched structure (FIG. 1B, lower right) is unnecessary to achieve the high specificity observed for capture reactions of BrdC-containing oligodeoxynucleotides.

Experimental and theoretical intensity ratios are compared in Tables IV and V. The theoretical intensity ratios were calculated using:

$$r_i/r_j = (q_i - 1) \cdot q_j / (q_j - 1) \cdot q_i \qquad (1)$$

The partition functions, $q_i$ and $q_j$, are close to 1 if the recipient ends are not saturated with displacer-linker duplexes. Then:

$$r_1/r_2(m=5) = \left(1 + \prod_{k=5}^{m} B_k + \Omega \sum_{i=5}^{m-1} \prod_{k=5}^{i} B_k \right) \Big/ (1 + \Omega) \qquad (2)$$

$$r_2(\text{all } m)/r_2(m=5) = \left(1 + \Omega \sum_{i=5}^{m} \prod_{k=5}^{i} B_k \right) \Big/ (1 + \Omega) \qquad (3)$$

Equation (2) was used for complete branch migration (Fragment B with displacer P-D-BrdC, P-D, MedC or P-D-dC). Equation (3) applied to all branch migration terminated by a mismatch at position M+1. For these calculations, $\Omega > 2$, $B_k = 1.7-1.9$ for BrdC and $B_k = 1$ for dC.

$B_k$ is the relative association constant for base pair k. $B_k$ is usually 1. For BrdC, $B_k = 1.7-1.9$ as determined in Example 2. Similarly for MedC, $B_k = 1.5-1.7$. The excellent qualitative agreement between theory and experiment suggests that the theory may be used for the design of displacer molecules.

Example 10

Linker Capture at 5' Ends

For capture at a 5' overhang, the directions of the displacer and linker strands were reversed, with the linker forming a duplex with the 3' portion of the displacer sequence which lacks homology to the recipient duplex.

Plasmid pALA-D-G3 is a pUC19 clone containing a 3.2 kb genomic fragment of human ALA-D. Oligodeoxynucleotides E-D-BrdC and X-D-BrdC were synthesized as displacers for branch migration at the unique EcoRI and XmaI, respectively. The same linker, E-L-dC (X-L-dC) was employed for both displacers.

pALA-D-G3 was digested with either EcoRI or XmaI and a second restriction endonuclease to produce convenient sizes of recipient fragments. This product was mixed with PstI plus RsaI digested pALA-D (Example 4) and capture reactions were carried out with equimolar P-L-dC and E-L-dC and 400 nM P-D-BrdC and either E-D-BrdC or X-D-BrdC.

The linker capture reactions were performed as described in Example 8, using 25 U/mL T4 DNA ligase, and analyzed using the gel-shift analysis illustrated in FIG. 2. The half-time for linker capture was 5' at EcoRI (0% G+C 5' overhang) and 20' at XmaI (100% G+C 5' overhang) when the half-time for linker capture in the same reaction 5' for PstI (50% G+C 3' overhang). Thus, the linker capture method may be applied to either 5' or 3' overhangs and overhangs of all possible G+C percent.

pALA-D was cut with SmaI, which produces blunt ends, and a second enzyme, and a capture reaction was carried out using X-D-BrdC and Sm-L-dC. Linker capture was observed, although the rate was more than two orders of magnitude slower than linker capture at recipient ends with 3' or 5' overhangs.

Example 11

Selective Cloning of Branch Migration Structures

The product of a branch migration-mediated capture reaction similar to those described in the previous examples was ligated into a vector and used to transform *E. coli* using standard cloning techniques, such as those described by Maniatis, et al. (1982).

The plasmid, pALA-D, was digested with PstI leading to 2771 and 1037 nt fragments. The 2771 pUC9-containing fragment was inactivated as a cloning vector by digestion with SmaI, which leads to two blunt-ended fragments. Each end of the 1037 nt fragment terminated in a Pst 1 site, one of which was the same as the Pst 1 site in fragment B. The branch migration-mediated capture reaction was carried out as described in Examples 7 and 8 using P-D-BrdC and P-L-dC. The products were ligated Into pUC19 digested with SphI and PstI, both of which cut in the polylinker region of the vector. The SphI end contained a 3'-overhang complementary to the overhang created by the capture of the displacer-linker duplex.

Figure 5:
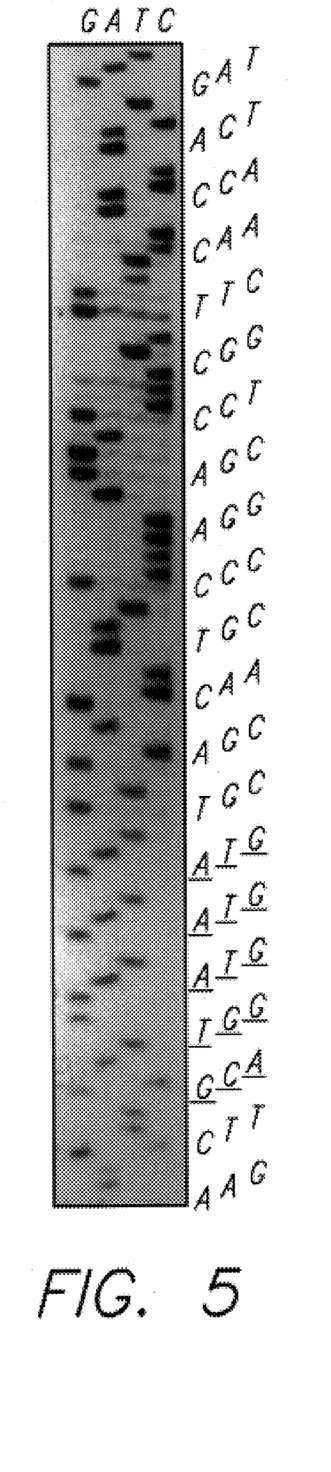
FIG. 5 depicts the autoradiogram of a sequencing gel showing the region of incorporated displacer (bold) and linker (underlined) sequences.

Four independent plasmid clones were digested by various restriction endonucleases and shown to have the patterns expected for linker incorporation following electrophoretic analysis of the resulting restriction digestion products. One of these clones was selected for further analysis using standard double-stranded DNA sequencing techniques. The autoradiogram of the sequencing gel depicted in FIG. 5 confirms the identity of the cloned insert as being the product resulting from branch migration-mediated capture and linker ligation. These results suggest that E. coli contain polymerases and nucleases capable of handling both BrdC substitutions and branched structures.

Thus, the branch migration product obtained according to the methods of this invention can be cloned directly using standard cloning techniques. Neither the presence of BrdC, nor the presence of a branched structure interfered with the cloning process.

Example 12

Branch Migration Mediated Labeling and Partial Digest Mapping

The plasmid pMS19 was constructed by inserting PMS-ES/PMS-SE and PMS-NH/PMS-HN into the EcoRI and HindIII sites, respectively, of pUC19 in the order indicated in Table I. The insertions destroyed the EcoRI and HindIII sites adjacent to the plasmid and inserted adjacent BglII (AGATCT) sites at each end of the expanded linker region. The new polylinker contains an SfiI site, a branch migration target sequence, the entire polylinker of pUC19, a different branch migration target sequence, and a NotI site.

Figure 6:
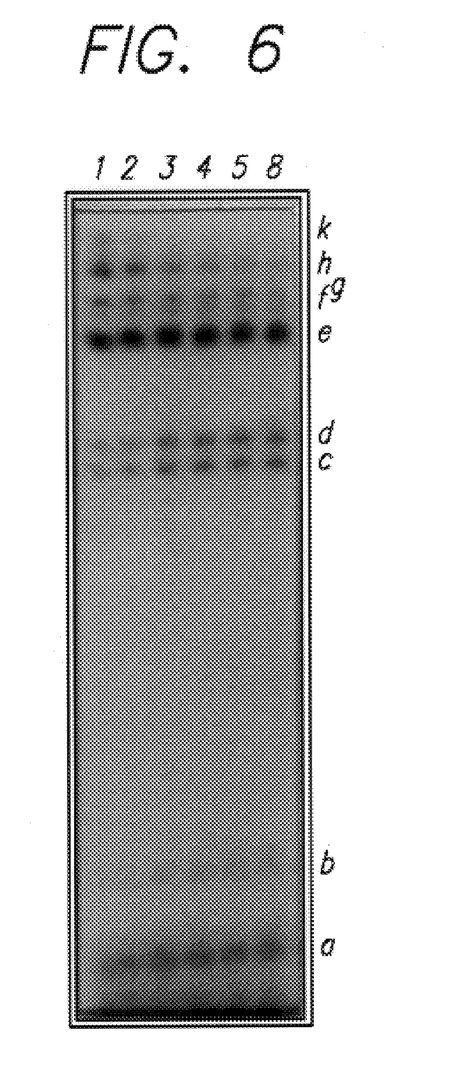
FIG. 6 depicts BCR using pALAD-G4, a derivative of pMS19 containing a genomic fragment of human ALAD, and displacer-linker duplex S-D-BrdC and S-L-dC was followed by partial digestion with Sau3A1. Lanes 1, 2, 3, 4, 5 and 8: partial digestion products formed at 1, 2, 3, 4, 5 and.8 minutes, respectively. Bands a–k are partial digest bands of the sizes expected: 300, 406, 1538, 1598, 2706, 2731, 2748, 3198, and multiple large bands produced by sites within the vector, respectively.

Using the BglII sites, this entire region expanded polylinker has been cloned into unique BamHI sites in other vectors including a cosmid vector. The reading frame was maintained so that pMS19 produces blue colonies when grown with IPTG and X-gel. A 3.6 kb EcoRI-HindIII genomic fragment of human ALA-D, the sequence of which had previously been determined, was cloned into the polylinker of pMS19 to produce the plasmid pMS19-G4.

pMS19-G4 was digested with NotI and SfiI. The product was end-labeled by branch migration mediated capture of $^{32}$p-labeled linker (SfiI) or displacer (NotI) using S-D-BrdC and S-L-dC to label the SfiI site or N-D-BrdC and N-L-dC to label the NotI site. This product was digested for various times with Sau3A1 and the products were analyzed by agarose gel electrophoresis. An autoradiogram of mapping at the SfiI end of the cloned fragment is depicted in FIG. 6. The resultant Sau3A1 map agreed with the known DNA sequence.

Because the melting temperature of the linker-displacer duplex is not critical for the branch migration process, labeling is not limited to radioactive labels, but may be extended to include a wide variety of labels permitting either detection or affinity purification of a labeled fragment. Thus, specific branch migration mediated labeling of restriction fragments may be applied to a wide variety of mapping and isolation techniques.

Example 13

Formation of Triple Helices

The target DNA used in Examples 13–14 was plasmid pMS19, described in Example 12.

Superhelical pMS19 DNA was mixed with an equal quantity of pMS19 which had been linearized by cleavage with EcoRI. Aliquots of this DNA mixture (20 μg/ml) were mixed with either $^{32}$P-labeled BT-D-MedC-1 (1 μg/ml) or $^{32}$P-labeled BO-D-MedC-1 (1 μg/ml) oligodeoxynucleotide in 100 mM sodium citrate, pH 4.8, at room temperature and allowed to cool to 4° C. BT-D-MedC-1 and BO-D-MedC-1 both contained sequences capable of forming a branch-migrated structure, whereas only BT-D-MedC-1 contained the polypyrimidine sequence capable of participating in triple helix formation.

The products of the incubation were separated by electrophoresis at 4° C. In a 1.2% agarose gel in 100 mM sodium citrate, pH 4.8. The gel was dried for autoradiography. Both the superhelical and the linear forms of pMS19 stably bound $^{32}$P-labeled BT-D-MedC-1. Neither the superhelical nor the linear form stably bound $^{32}$P-labeled BO-D-MedC-1.

Thus, the ability to form a branch-migration product, even at a low pH where branch migration is most favored, was not sufficient for forming a stable complex with linear or even with superhelical DNA. On the other hand, a stable triple-helical product was formed with both linear and superhelical DNA when the polypyrimidine sequence was present.

Example 14

Coupling of Branch Migration with Triple Helix Formation

The recipient plasmid was pMS19 cut with NciI and SalI. SalI is an enzyme producing a 5' overhang. Displacer molecules were either $^{32}$P-labeled BO-D-MedC-1 or $^{32}$P-labeled BT-D-MedC-1. The linker molecule was BT-L-dC-1. Displacer-linker duplexes were formed as described in Example 6, hybridized as described in Example 7 and ligated as described in Example 8 except that the concentration of displacer-linker duplex was 0.2 μM, the solvent was 25 mM tris-acetate, pH 6.8, 10 mM NaCl, 1 mM spermine, 1 mM DTT, 10 mM MgCl$_2$, 1 mM ATP.

TABLE I

| Oligodeoxynucleotides | |
|---|---|
| A. Thermodynamics and Kinetics | |
| 14-dC-S | ATG CAG CTA AGT CA |
| 14-dC-A | TGA CTT AGC TGC AT |
| 14-BrdC-S | ATG CAG CTA AGT CA |
| 14-BrdC-A | TGA CTT AGC TGC AT |
| 14-MedC-S | ATG CAG CTA AGT CA |
| 14-MedC-A | TGA CTT AGC TGC AT |
| 12-dC-S | CAT GCA GCC CCA |
| 12-dC-A | TGG GGC TGC ATG |
| 12-BrdC-S | CAT GCA GCC CCA |

TABLE I-continued

Oligodeoxynucleotides

| | | | | | | | | | | |
|---|---|---|---|---|---|---|---|---|---|---|
| 12-MedC-S | | | | C̲A̲T̲ | G C̲A̲ | GC̲C̲ | C̲C̲A̲ | | | |
| 16-dC-A | | | | TGG | GGC | TGC | ATG | GCG | T | |
| 16-BrdC-S | | | | ACG | CCA | TGC | AGC | CCC | A | |

Nomenclature:
Oligodeoxynucleotide length — (dC, MedC, BrdC) — (S = sense; A = antisense).
C = 5'-Bromodeoxycytidine, C = 5'-Methyldeoxycytidine.

B. Linkers, Displacers and Targets

| | | | | | | | | | | | | | | | |
|---|---|---|---|---|---|---|---|---|---|---|---|---|---|---|---|
| PstI | | | GAT | GAT | GAT | GTG | CAG | C̲C̲A̲ | ATG | C̲C̲C̲ | CAG | GAG | C̲C̲C̲ | T | P-D-MedC |
| | | | GAT | GAT | GAT | GTG | CAG | CCA | AAG | CCC | CAG | GAG | CCC | T | P-D-BrdC-E(10) |
| | | | GAT | GAT | GAT | GTG | CAG | CCA | ATG | CCC | CAG | GAG | CCC | A | P-D-BrdC-E(24) |
| | | | GAT | GAT | GAT | GTG | CAG | CCA | ATG | CCC | CAG | GAG | CCC | T | P-D-BrdC |
| | G | TAC | CTA | CTA | CTA | C | | | | | | | | | P-L-dC |
| | | | | | | *G | CCA | ATG | CCC | CAG | GAG | CCC | T | | P-T-D |
| | | | | | AC | GTC | GGT | TAC | GGG | GTC | CTC | GGG | A | | P-T-L |
| EcoRI | | CCT | CGA | AGG | AGC | CTT | CCA | CAG | CCG | AAT | TGT | AGT | AGT | AGT | AAG CT E-D-BrdC |
| | | | | | | | | | CA | TCA | TCA | TCA | T | | E-L-dC |
| | | *CCT | CGA | AGG | AGC | CTT | CCA | CAG | CCG | | | | | | E-T-D |
| | | GGA | GCT | TCC | TCG | GAA | GGT | GTC | GGC | TTA | A | | | | E-T-L |
| XmaI (SmaI) | | TCT | CGG | CTC | ACT | GCA | ACG | TCC | GCC | TCC | CGG | GTA | GTA | GTA | GTA X-D-BrdC |
| | | | | | | | | | | | CAT | CAT | CAT | CAT | X-L-dC |
| | | | | | | | | | CC | CAT | CAT | CAT | CAT | | Sm-L-dC |
| | | *TCT | CGG | CTC | ACT | GCA | ACG | TCC | GCC | TC | | | | | X-T-D |
| | | AGA | GCC | GAG | TGA | CGT | TGC | AGG | CGG | AGG | GCC | | | | X-T-L |
| SfiI | | GTA | GTA | GTA | GTA | CCC | CGG | CCA | CAC | ACA | CAC | ACA | CAC | GA | | S-D-BrdC |
| | | CAT | CAT | CAT | CAT | | | | | | | | | | S-L-dC |
| NotI | | CTC | TCT | CTC | TCT | CTC | TCT | GCG | GCC | GTA | GTA | GTA | GTA | | | N-D-BrdC |
| | | | | | | | | | | CAT | CAT | CAT | CAT | | N-L-dC |

Nomenclature:
Oligodeoxynucleotides are named x-y-2 where:
x = restriction site (first letter only)
y = function (displacer, linker or target)
z = composition (BrdC, MedC, dC) or polarity (displacer or linker side)
E(N) = error at position N (a mismatch) if present

C. Plasmid pMS19 construction

| | | | | | | | | | | | | | | | |
|---|---|---|---|---|---|---|---|---|---|---|---|---|---|---|---|
| EcoRI | AAT | TGA | GAT | CTG | GCC | ACC | CCG | GGG | ACA | CAC | ACA | CAC | ACG | | | PMS-ES |
| | CT | CTA | GAC | CGG | TGG | GGC | CGG | TGT | GTG | TGT | GTG | TGC | TTA | A | | PMS-SE |
| HindIII | AGC | TTG | CTC | TCT | CTC | TCT | CTC | TCT | GCG | GCC | GCT | TTT | AGA | TCT | C | PMS-NH |
| | AC | GAG | AGA | GAG | AGA | GAG | AGA | CGC | CGG | CGA | AAA | TCT | AGA | G | TCG A | PMS-HN |

Nomenclature:
Oligodeoxynucleotides are named x-y where:
x = function. (PMS)
y = orientation in product (e.g. ES is EcoRI to SfiI)

D. Triplex-formation (at SalI in pMS19)

| | | | | | | |
|---|---|---|---|---|---|---|
| TCTCTCTCTCTCTCTC | C̲ | AAGC̲TT | GC̲ATGC̲ | C̲TGC̲AG | GTC̲GAC̲ | TCAATGATTCCC | BT-D-MedC(1)-1 |
| | | | | | G | AGTTACTAAGGG | BT-L-dC-1 |
| | C̲ | AAGC̲TT | GC̲ATGC̲ | C̲TGC̲AG | GTC̲GAC̲ | TCAATGATTCCC | B0-D-MedC(1)-1 |
| | | | | | G | AGTTACTAAGGG | BT-L-dC-1 |

Nomenclature:
Oligodeoxynucleotide are named x-y-z where
x = BT if both branch migration and triplex formation are possible,
x = B0 if only branch migration is possible;
y = composition (dC, MedC or BrdC) in the branch migration region (1) and/or triplex forming region (2);
z = laboratory index.

TABLE II

Bromodeoxycytidine and Methyldeoxycytidine Thermodynamics

| Oligodeoxynucleotides | $t_m$ In 1 M Na$^+$, C = 6 μM | | |
|---|---|---|---|
| | pH 4 | pH 7 | pH 10 |
| 14-dC-A + 14-dC-S | | 57° | |
| 14-dC-A + 14-BrdC-S | | 63° | |
| 14-dC-S + 14-BrdC-A | | 62.5° | |
| 14-BrdC-A + 14-BrdC-S | | 65° | |
| 12-dC-A + 12-dC-S | 60° | 53.5° | 50° |
| 12-dC-A + 12-BrdC-S | 70° | 69.5° | 54° |

TABLE II-continued

Bromodeoxycytidine and Methyldeoxycytidine Thermodynamics

| Oligodeoxynucleotides | $t_m$ In 1 M Na$^+$, C = 6 μM | | |
|---|---|---|---|
| | pH 4.7 | pH 7 | pH 9.6 |
| 14-dC-A + 14-C-S | | 57° | |
| 14-dC-A + 14-MedC-S | | 60° | |
| 14-dC-S + 14-MedC-A | | 59.5° | |
| 14-MedC-A + 14-MedC-S | | 64.5° | |
| 12-dC-A + 12-CL-S | 50° | 60° | 47.5° |
| 12-dC-A + 12-MedC-S | 55° | 67° | 50.5° |

TABLE III

Temperature Dependence of Displacement
Rates with BrdC-Containing Displacers

A. Blunt ends

| Oligodeoxynucleotides | Temp (° C.) | Half-time (min) for displacement with 12-BrdC-S at: | | |
|---|---|---|---|---|
| | | 101 μM | 20 μM | 4 μM |
| 12-dC-S* (C = 0.25 μM) + | 37 | 2 | 4–8 | 16–32 |
| 12-dC-A (C = 0.75 μM) | 32 | 4–8 | 8–16 | 32 |
| | 27 | 4–8 | 32–4 | 128–256 |

B. Overhangs

| Oligodeoxynucleotides | (° C.) | Half-time (min) for displacement with 16-BrdC-S at: | |
|---|---|---|---|
| | | 3 μM | 0.57 μM |
| 12-dC-S* (C = 0.25 μM) + | 37 | <1 | 4–8 |
| 16-dC-A (C = 0.57 μM) | 32 | <1 | 16–32 |
| | 27 | <1 | 2–4 |
| | 22 | – | <1 |

C. Effect of Linkers

| Site | Overhang | G + C % | Half time for displacement (minutes) | |
|---|---|---|---|---|
| | | | No linker | Linker |
| EcoRI | 5' | 0 | 60 | 6 |
| Pstl | 3' | 50 | 8 | <1 |
| Xmal | 5' | 100 | 8–16 | <1 |

*5'-$^{32}$P-labeled
CONDITIONS:
Ligase buffer (pH = 7); 37° C.; 10 μL per reaction.
Target: Kinased strand 10 ng, Unlabeled strand 30 ng.
Displacer: 150 ng; Linker (if present): large molar excess.
Displacer concentration = 1 μM.

TABLE IV

Linker Capture

| | Displacer | | | | | |
|---|---|---|---|---|---|---|
| | 34-BrdC-D | | 34-MedC-D | | 34-dC-D | |
| Fragment: | Experimental | Calculated | Experimental | Calculated | Experimental | Calculated |
| A | 16 | 9 | 10 | 7 | 4 | 4 |
| B | 384 | 344 | 150 | 144 | 16 | 15 |
| D | 1* | 1* | 1* | 1* | 1* | 1* |

*by definition

TABLE V

Linker Capture with Mismatches

| Displacer | Relative yield (Fragment B/Fragment A) | |
|---|---|---|
| | Experimental | Calculated |
| P-D-BrdC | 24 | 29 |
| P-D-BrdC-E(10) | 1 | 1 |
| P-D-BrdC-E(24) | 24 | 39 |

The effective ligase activity was determined by comparing the rate of circularization of EcoRI linerized pMS19 in the solvent above compared with ligase buffer, where 50% of the molecules are circularized in 25 minutes at 100 U/ml. The ligase activity determined was approximately 0.5 U/ml.

Figure 7:
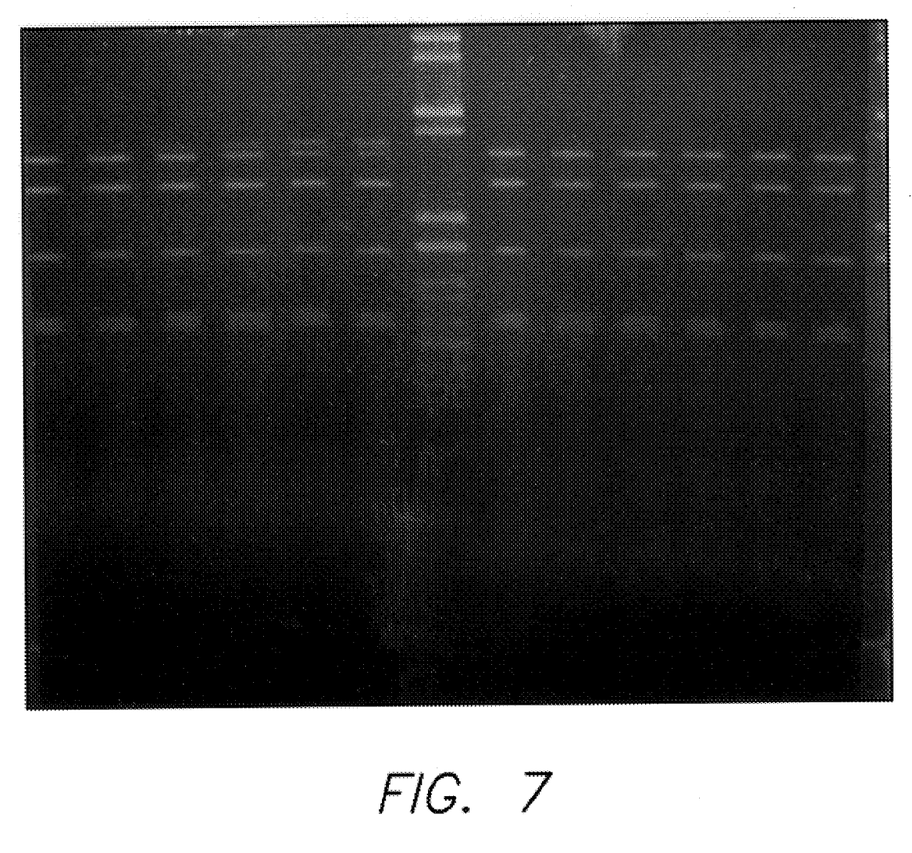
FIG. 7 depicts triplex enhanced branch-migration mediated linker capture. Lanes 1–6: pMS19, cut with NciI and SalI, incubated with BT-D-MedC-1, BT-L-dC-1 and T4 DNA ligase as described in the text, for 0, 1, 3, 10, 30 and 120 min. Lane 7: Molecular weight markers of lambda DNA cut with AvaII Lanes 8–13: pMS19, cut with NciI and SalI, incubated with BO-D-MedC-1, BT-L-dC-1 and T4 DNA ligase as described in the text, for 0, 1, 3, 10, 30 and 120 min.

FIG. 7 depicts the a fluorogram of the branch migration experiments. After 30 minutes, 50% of the recipient duplexes have captured a linker in the presence of BT-D-MedC-1. The rate of linker capture with BT-D-MedC-1 was greater than thirty times that predicted for the ligase activity and the concentrations of displacer-linker duplex using the method in Example 8.

The gel was dried for autoradiography. The branch migration products visible in the fluorogram in lanes 4–6 were visible in the autoradiogram, demonstrating that the new fluorogram bands represent branch migration-mediated capture products.

After overnight incubation, branch migration products could be seen with both displacers with 50% yield of ligated product with BO-D-MedC-1. Thus, the inclusion of a particular, unmodified, triplex-forming region on displacer BT-D-MedC-1, but not BO-D-MedC-1, stabilized the branch migration intermediates by greater than 30-fold.

Although the foregoing invention has been described in some detail by way of illustration and example for clarity of understanding, it will be obvious that certain changes and modifications may be practiced within the scope of the following claims.

We claim:

1. In a method of forming a non stable complex between one strand of a recipient polydeoxynucleotide sequence and a displacer sequence of single stranded DNA where the displacer sequence is at least partially complementary to such strand of a recipient polydeoxynucleotide sequence, the improvement comprising stabilizing the complex.

2. The method of claim 1 wherein the nonstable complex is stabilized by the presence of at least one modified nucleotide in the displacer strand.

3. The method of claim 1 wherein the complex is stabilized by forming a DNA triplex between the displacer sequence and the recipient duplex.

4. The method of claim 1 wherein the displacer strand comprises a nucleotide sequence and a sequence specific DNA binding moiety that does not significantly melt the recipient DNA duplex at the site to which it attaches.

5. The method of claim 1 wherein the displacer sequence is duplexed with a linker in a displacer-linker duplex wherein the displacer-linker duplex comprises two strands;

1. a displacer strand of which a portion comprises nucleotides complementary to one strand of a recipient polydeoxynucleotide duplex and a portion which comprises a sequence complementary to and hybridized with a linker strand, and 2. a linker strand complementary to and hybridized with the displacer strand.

6. An oligo- or polydeoxynucleotide displacer-linker duplex which is capable of initiating branch migration at the end of a recipient polydeoxynucleotide duplex without the prior formation of a stable hybrid with such recipient polydeoxynucleotide duplex, which displacer-linker duplex comprises two strands;

a. a displacer strand of which a portion comprises nucleotides complementary to one strand of a recipient polydeoxynucleotide duplex and a portion which comprises a sequence complementary to and hybridized with a linker strand, and b. a linker strand complementary to and hybridized with the displacer strand.

7. The displacer-linker duplex of claim 6 which can initiate branch migration at a restriction endonuclease cleavage site.

8. The displacer-linker duplex of claim 6 which can hybridize to and initiate branch migration adjacent to a 3' or 5' single stranded extension on the recipient polydeoxynucleotide duplex.

9. The displacer-linker duplex of claim 6 wherein at least one of the nucleotides complementary to one strand of the recipient polydeoxynucleotide duplex is modified to increase the stability of the hybrid displacer-recipient duplex.

10. The displacer-linker duplex of claim 6 wherein at least one of the nucleotides complementary to one strand of a recipient polydeoxynucleotide duplex is modified to increase the melting temperature of the hybrid displacer-recipient duplex.

11. The displacer-linker duplex of claim 9 wherein the modified nucleotide is selected from the group consisting of modified nucleotides which increase the association constant with the complementary deoxynucleotide by at least about 20 percent.

12. The displacer-linker duplex of claim 9 wherein the modified nucleotide is selected from the group consisting of 5-halogenated pyrimidine nucleotides, 5-methyldeoxycytidine, diaminopurine deoxynucleotide, ribonucleotides, and 2'-alkylated ribonucleotides.

13. The displacer-linker duplex of claim 9 wherein the modified nucleotide is a 5-halogenated pyrimidine nucleotide.

14. The displacer-linker duplex of claim 9 wherein the modified nucleotide is 5-bromodeoxyuridine.

15. The displacer-linker duplex of claim 9 wherein the modified nucleotide is 5-methyldeoxycytidine.

16. The displacer-linker duplex of claim 6 which contains a modification which permits detection of the displacer-recipient hybrid.

17. The modified displacer-linker duplex of claim 16 wherein the modification is selected from the group consisting of radioactive labels, fluorescent labels and targets for detection, including biotin moieties, enzymes and phosphorothioate linkages.

18. The modified displacer-linker duplex of claim 16 wherein the modification is present in the linker.

19. The displacer-linker duplex of claim 6 which contains a modification which allows capture of the displacer-recipient hybrid by affinity chromatography.

20. The displacer-linker duplex of claim 19 wherein the modification is selected from the group consisting of biotin moieties and phosphorothioate linkages.

21. The displacer-linker duplex of claim 19 wherein the modification is present in the linker.

22. The displacer-linker duplex of claim 6 which also comprises a 5' or 3' single-stranded extension complementary to a 5' or 3' single-stranded extension resulting from the digestion of a polydeoxynucleotide duplex with a restriction endonuclease.

23. An artificially constructed polydeoxynucleotide hybrid comprising a naturally occurring recipient polydeoxynucleotide duplex hybridized to the displacer-linker duplex of any of claims 6–22.

24. The artificially constructed polydeoxynucleotide hybrid of any of claims 6–22 wherein the linker strand is covalently linked to one of the strands of the recipient duplex.

25. A method of modifying a recipient polydeoxynucleotide duplex by contacting such recipient polydeoxynucleotide duplex with a displacer-linker duplex under conditions that permit the formation of a hybrid polydeoxynucleotide duplex, wherein
the displacer-linker duplex comprises two strands;
1. a displacer strand of which a portion comprises nucleotides complementary to one strand of a recipient polydeoxynucleotide duplex and a portion which comprises a sequence complementary to and hybridized with a linker strand, and
2. a linker strand complementary to and hybridized with the displacer strand.

26. The method of claim 25 wherein the recipient duplex terminates in a 3' or 5' single stranded extension and the displacer strand contains a sequence complementary to the extension.

27. The method of claim 25 where the hybrid is stabilized after formation of the hybrid polynucleotide duplex.

28. The method of claim 27 wherein the hybrid is stabilized by covalently linking the linker strand of the displacer-linker duplex to the strand of the recipient duplex complementary to the displacer strand.

29. The method of claim 28 wherein the covalent link is a phosphodiester linkage.

30. The method of claim 28 wherein the hybrid is stabilized by ligating the linker strand of the displacer-linker duplex to the strand of the recipient duplex complementary to the displacer strand using T4 DNA ligase.

31. The method of claim 25 wherein at least one of the nucleotides complementary to one strand of the recipient polydeoxynucleotide duplex is a modified nucleotide which increases the stability of the hybrid displacer-recipient duplex.

32. The method of claim 25 wherein at least one of the nucleotides complementary to one strand of the recipient polydeoxynucleotide duplex is a modified nucleotide which increases the melting temperature of the hybrid displacer-recipient duplex.

33. The method of claim 31 wherein the modified nucleotide is selected from the group consisting of modified nucleotides which increase the association constant with the complementary deoxynucleotide by at least about 20 percent.

34. The method of claim 31 wherein the modified nucleotide is selected from the group consisting of 5-halogenated pyrimidine nucleotides, 5-methyldeoxycytidine, diaminopurine deoxynucleotide, ribonucleotides, and 2'-alkylated ribonucleotides.

35. The method of claim 31 wherein the modified nucleotide is a 5-halogenated pyrimidine nucleotide.

36. The method of claim 31 wherein the modified nucleotide is 5-bromodeoxycytidine.

37. The method of claim 31 wherein the modified nucleotide is 5-methyldeoxycytidine.

38. The method of claim 31 wherein from about 10 percent to about 80 percent of the nucleotides complementary to one strand of the recipient polydeoxynucleotide duplex are modified nucleotides.

39. A method of labelling an artificially constructed nucleic acid hybrid of a naturally occurring recipient polydeoxynucleotide duplex hybridized to a displacer-linker duplex which is capable of initiating branch migration at the end of the recipient polydeoxynucleotide duplex without the prior formation of a stable hybrid with such recipient polydeoxynucleotide duplex, which displacer-linker duplex comprises two strands:

1. a displacer strand of which a portion comprises nucleotides complementary to one strand of a recipient polydeoxynucleotide duplex and a portion which comprises a sequence complementary to and hybridized with a linker strand, and
2. a linker strand complementary to and hybridized with the displacer strand, which method of labelling comprises modifying the displacer-linker duplex to incorporate therein a modification which permits detection of the artificially constructed nucleic acid hybrid.

40. The method of claim 39 wherein the displacer-linker duplex is modified prior to hybridization with the naturally occurring recipient polydeoxynucleotide duplex.

41. The method of claim 39 wherein the linker strand of the displacer-linker duplex is covalently linked to the strand of the naturally occurring recipient polydeoxynucleotide duplex complementary to the displacer strand.

42. The method of claim 39 wherein the modification is selected from the group consisting of radioactive labels, fluorescent labels, enzymes and chemical labels including biotin moieties and phosphorothioate linkages.

43. The method of claim 39 wherein the modification is selected from the group consisting of targets for affinity chromatography.

44. The method of claim 43 wherein the modification is selected from the group consisting of biotin moieties and phosphorothioate linkages.

45. The method of claim 39 wherein the modification comprises a 5' or 3' single-stranded extension of the displacer-linker duplex, which extension
   1) is unaffected by formation of the displacer-linker-recipient polydeoxynucleotide duplex hybrid, and
   2) is a target for attachment to polydeoxynucleotide duplexes containing complementary 5' or 3' single stranded extensions.

46. The method of claim 39 used to label one end of a cloned deoxynucleotide insert in a vector.

47. The method of claim 46 where the vector is a plasmid vector.

48. The method of claim 46 where the vector is a cosmid vector.

49. The method of claim 46 where the vector is a yeast artificial chromosome vector.

50. In a method of restriction endonuclease mapping of an insert, the improvement comprising labelling the insert by the method of claim 40.

51. In a method of capture of an artificially constructed nucleic acid hybrid by affinity chromatography, the improvement comprising labelling the hybrid by the method of claim 39.

52. In a method of enriching a recipient polydeoxynucleotide duplex in a population of polydeoxynucleotide duplexes, the improvement comprising labelling the recipient polydeoxynucleotide duplex by the method of claim 39.

53. In a method of covalently attaching a restriction endonuclease linker onto a recipient polydeoxynucleotide duplex, the improvement comprising labelling the resulting hybrid by the method of claim 39.

54. In a method of selectively cloning a recipient polydeoxynucleotide duplex by covalently attaching a restriction endonuclease linker onto such recipient polydeoxynucleotide duplex, the improvement comprising labelling the hybrid by the method of claim 39.

55. In a method of isolating clones of contiguous polydeoxyribonucleotide duplexes by covalently attaching a restriction endonuclease linker onto the duplexes, the improvement comprising labelling the clones by the method of claim 39.

56. An oligo- or polydeoxynucleotide displacer which is capable of binding to a recipient polydeoxynucleotide duplex which displacer comprises
   1) a first sequence which is capable of initiating triple helix formation, and which comprises
      a) at least six consecutive pyrimidine bases or
      b) at least seven bases where at least six of the bases are pyrimidine bases and the seventh base is guanine, and
   2) a second sequence proximate to such first sequence which is complementary to and runs antiparallel to the second strand of the recipient duplex and which is capable of initiating branch migration proximate to the triple helix.

57. The displacer of claim 56 wherein the second sequence is adjacent to the first sequence.

58. The displacer of claim 56 wherein the second sequence is separated from the first sequence by from 1 to 5 intervening moieties.

59. The displacer of claim 58 wherein the intervening moieties are nucleotides.

60. The displacer of claim 59 wherein at least one of the moieties is a modified nucleotide.

61. The displacer of claim 58 wherein wherein one of the intervening moieties has an intercalating agent covalently attached.

62. The displacer of claim 56 wherein at least one of the nucleotides complementary to one strand of the recipient polydeoxynucleotide duplex is modified to increase the stability of the displacer-recipient complex.

63. The displacer of claim 56 wherein at least one of the nucleotides complementary to one strand of a recipient polydeoxynucleotide duplex is modified to increase the melting temperature of the displacer-recipient complex.

64. The displacer of claim 62 wherein the modified nucleotide is selected from the group consisting of modified nucleotides which increase the association constant with the complementary deoxynucleotide by at least about 20 percent.

65. The displacer of claim 62 wherein the modification is in the first sequence.

66. The displacer of claim 65 wherein the modified nucleotide is a 5-halogenated pyrimidine nucleotide.

67. The displacer of claim 65 wherein the modified nucleotide is selected from the group consisting of 5-bromodeoxyuridine and 5-methyldeoxycytidine.

68. The displacer of claim 62 wherein the modification is in the second sequence.

69. The displacer of claim 68 wherein the modified nucleotide is selected from the group consisting of 5-halogenated pyrimidine nucleotides, 5-methyldeoxycytidine, diaminopurine deoxynucleotide, ribonucleotides and a 2'-alkylated ribonucleotides.

70. The displacer of claim 68 wherein the modified nucleotide is a 5-halogenated pyrimidine nucleotide.

71. The displacer of claim 68 wherein the modified nucleotide is 5-bromodeoxyuridine.

72. The displacer of claim 68 wherein the modified nucleotide is 5-methyldeoxycytidine.

73. The displacer of claim 56 which further comprises at least one moiety attached to a terminus of the oligo or polydeoxynucleotide, which moiety confers endonuclease resistance to the terminus to which it is attached.

74. The displacer of claim 73 wherein the moiety is attached to the deoxyribose moiety of a terminal nucleotide.

75. The displacer of claim 74 wherein the moiety is indirectly attached to the deoxyribose moiety of a terminal nucleotide.

76. The displacer of claim 73 wherein the moiety is attached to the hydroxyl group of a terminal nucleotide.

77. The displacer of claim 73 wherein the moiety is attached to the phosphate moiety of a terminal nucleotide.

78. The displacer of claim 73 where the moiety is selected from the group consisting of intercalating agents, isoureas, carbodiimides and N-hydroxybenzotriazoles.

79. The displacer of claim 76 wherein the moiety is a methylthiophosphonate.

80. The displacer of claim 73 wherein the moiety is a selected from the group consisting of polypeptides and proteins.

81. The displacer of claim 73 wherein the moiety is a 2',3'-dideoxyribose nucleotide attached to the 3'-terminal deoxyribonucleotide through a phosphodiester linkage.

82. The displacer of claim 81 wherein the 2',3'-dideoxyribose nucleotide is a modified 2',3'-dideoxyribose nucleotide.

83. The displacer of claim 56 which contains a modification which permits detection of the displacer-recipient hybrid.

84. The modified displacer of claim 83 wherein the modification is selected from the group consisting of radioactive labels, fluorescent labels, enzymes and targets for detection, including biotin moieties and phosphorothioate linkages.

85. The displacer of claim 56 which contains a modification which allows capture of the displacer-recipient hybrid by affinity chromatography.

86. The displacer of claim 85 wherein the modification is selected from the group consisting of biotin moieties and phosphorothioate linkages.

87. An artificially constructed polydeoxynucleotide hybrid comprising a naturally occurring recipient polydeoxynucleotide duplex hybridized to the displacer of either one of claims 57–86.

88. An method of modifying a recipient polydeoxynucleotide duplex comprising contacting such recipient polydeoxynucleotide duplex with the displacer of claim 57 under conditions that permit the formation of a complex.

89. The method of claim 88 wherein at least one of the nucleotides complementary to one strand of the recipient polydeoxynucleotide duplex is modified to increase the stability of the displacer-recipient complex.

90. The method of claim 88 wherein at least one of the nucleotides complementary to one strand of a recipient polydeoxynucleotide duplex is modified to increase the melting temperature of the displacer-recipient complex.

91. The method of claim 88 wherein the modified nucleotide is selected from the group consisting of modified nucleotides which increase the association constant with the complementary deoxynucleotide by at least about 20 percent.

92. The method of claim 88 wherein the modification is in the first sequence of the displacer of claim 57.

93. The method of claim 92 wherein the modified nucleotide is selected from the group consisting of 5-bromodeoxyuridine and 5-methyldeoxycytidine.

94. The method of claim 88 wherein the modification is in the second sequence of the displacer of claim 57.

95. The method of claim 94 wherein the modified bases are selected from the group consisting of 5-halogenated pyrimidine nucleotides, 5-methyldeoxycytidine, diaminopurine deoxynucleotide, ribonucleotides, and 2'-alkylated ribonucleotides.

96. The method of claim 94 wherein the modified nucleotide is a 5-halogenated pyrimidine nucleotide.

97. The method of claim 94 wherein the modified nucleotide is 5-bromodeoxyuridine.

98. The method of claim 94 wherein the modified nucleotide is 5-methyldeoxycytidine.

99. The method of claim 88 wherein the displacer contains at least one moiety attached to a terminus of the oligo or polynucleotide, which moiety confers endonuclease resistance to the terminus to which it is attached.

100. The method of claim 99 wherein the moiety is attached to the deoxyribose moiety of a terminal nucleotide.

101. The method of claim 100 wherein the moiety is indirectly attached to the deoxyribose moiety of a terminal nucleotide.

102. The method of claim 99 wherein the moiety is attached to the hydroxyl group of a terminal nucleotide.

103. The method of claim 99 wherein the moiety is attached to the phosphate moiety of a terminal nucleotide.

104. The method of claim 99 where the moiety is selected from the group consisting of intercalating agents, isoureas, carbodiimides and N-hydroxybenzotriazoles.

105. The method of claim 101 wherein the moiety is a methylthiophosphonate.

106. The method of claim 99 wherein the moiety is a selected from the group consisting of polypeptides and proteins.

107. The method of claim 99 wherein the moiety is a 2',3'-dideoxyribose nucleotide attached to the 3'-terminal deoxyribonucleotide through a phosphodiester linkage.

108. The method of claim 107 wherein the 2',3'-dideoxyribose nucleotide is a modified 2',3'-dideoxyribose nucleotide.

109. A method of labelling a displacer-recipient complex comprising contacting a recipient polydeoxynucleotide duplex with the displacer of claim 101 under conditions that permit the formation of a complex wherein the displacer contains a modification which will permit detection of the displacer-recipient complex.

110. The method of claim 109 wherein the modification is selected from the group consisting of radioactive labels, fluorescent and chemiluminescent labels, enzymes and targets for detection.

111. The method of claim 109 wherein the modification is selected from the group consisting of targets for affinity chromatography.

112. The method of claim 111 wherein the modification is selected from the group consisting of biotin moieties and phosphorothioate linkages.

113. In a method of capture of an artificially constructed nucleic acid hybrid by affinity chromatography, the improvement comprising modifying the hybrid by the method of claim 88.

114. In a method of enriching a recipient polydeoxynucleotide duplex in a population of polydeoxynucleotide duplexes, the improvement comprising labelling the recipient polydeoxynucleotide duplex by the method of claim 88.

115. In a method for the site specific addition, deletion or alteration of nucleotides in a recipient polydeoxynucleotide duplex, the improvement comprising modifying the duplex by the method of claim 88.

116. In a method of repairing a mutational lesion comprising replacing a naturally occurring strand of DNA with a modified strand of DNA, the improvement wherein the new strand is introduced to the naturally occurring duplex by the method of claim 88 and displaces the original strand.

* * * * *